United States Patent [19]

Comstock et al.

[11] Patent Number: 4,938,846
[45] Date of Patent: Jul. 3, 1990

[54] PREPARATION OF ANHYDROUS ALKANESULFONIC ACID

[75] Inventors: Perry D. Comstock, Wyandotte; Karen M. Keys, Southfield, both of Mich.

[73] Assignee: ATOCHEM, North America, Inc., Philadelphia, Pa.

[21] Appl. No.: 939,200

[22] Filed: Dec. 8, 1986

[51] Int. Cl.$^5$ .................... B01D 1/00; B01D 3/00
[52] U.S. Cl. ........................ 203/15; 159/13.1;
159/48.1; 159/49; 159/DIG. 16; 203/78;
203/80; 203/89; 203/90; 562/124
[58] Field of Search ............ 203/15, 80, 78, 89,
203/90; 202/236; 159/48.1, 13.1, 49, DIG. 16;
562/124

[56] References Cited

U.S. PATENT DOCUMENTS

| | | | |
|---|---|---|---|
| 2,518,639 | 8/1950 | Proell | 562/124 R |
| 2,523,490 | 9/1950 | Adams et al. | 260/513 R |
| 2,711,388 | 6/1955 | Mottern et al. | 203/15 |
| 3,509,206 | 4/1970 | Nielsen | 562/513 R |
| 4,028,072 | 6/1977 | Braun et al. | 202/202 |
| 4,035,242 | 7/1977 | Brandt | 203/15 |
| 4,450,047 | 5/1984 | Malzahn | 203/73 |
| 4,652,343 | 3/1987 | Sridhar | 260/513 R |

Primary Examiner—Virginia Manoharan

[57] ABSTRACT

A process for the removal of water from a lower alkanesulfonic acid-water mixture by causing the mixture to run down the internal walls of two vertical evaporator columns operated in series, is disclosed herein.

15 Claims, 1 Drawing Sheet

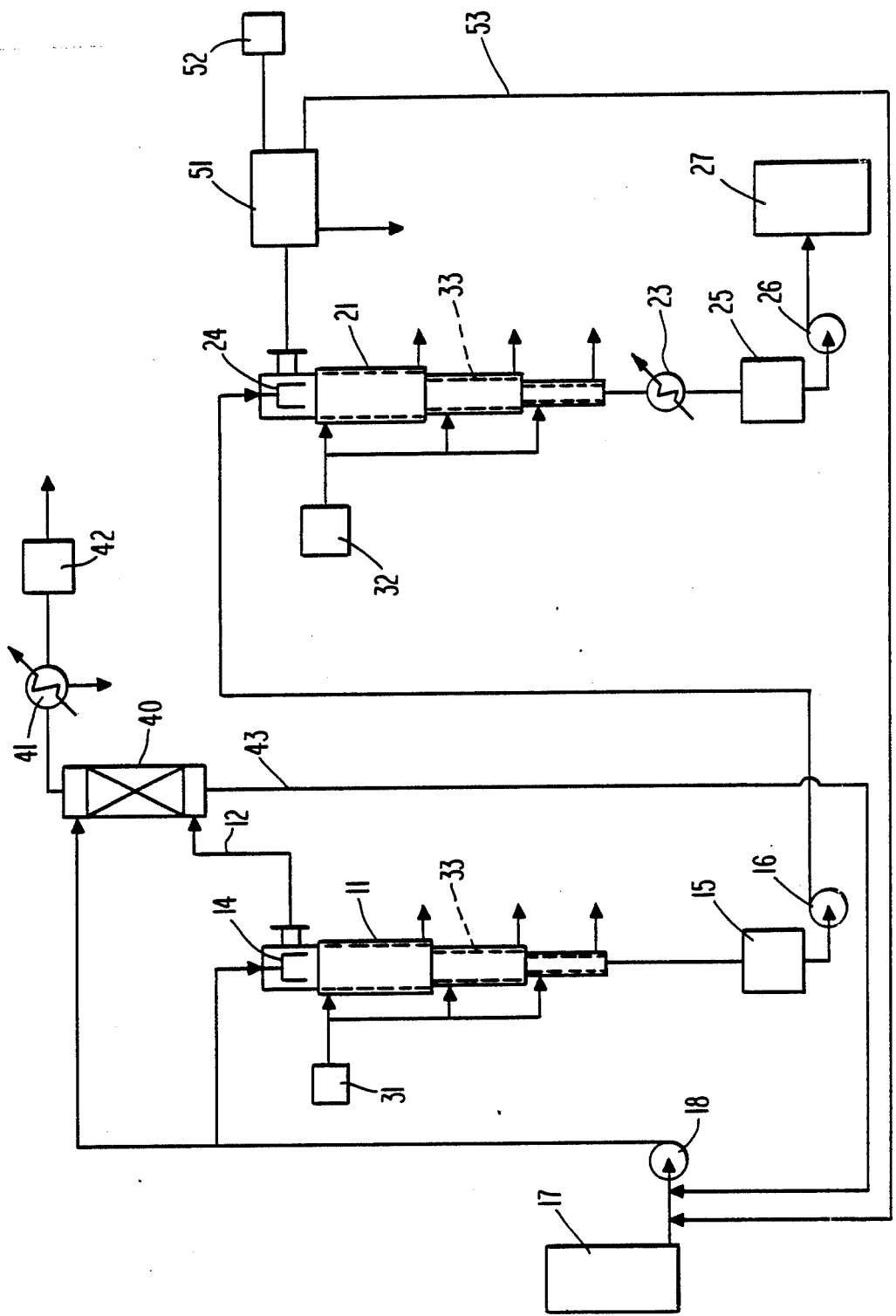

PREPARATION OF ANHYDROUS ALKANESULFONIC ACID

BACKGROUND OF THE INVENTION

In the manufacture of methanesulfonic acid, for example in processes of the type disclosed in U.K. Pat. No. 1,350,328, an aqueous product which normally contains between about 15-60% by weight and higher amounts of water is obtained. In order to prepare an anhydrous product (<2 wt. % water), useful, for example, as a reaction medium in the preparation of aromatic peroxy acids where excess water retards the reaction, the water must be removed from methanesulfonic acid while minimizing the formation of decomposition product e.g., methyl methanesulfonate, a known carcinogen. In the past, a two step distillative purification process[1] for lower alkanesulfonic acids was used. However, this practice led to products which were partially decomposed and contained undesirable amounts of water. More recently, a superior process has been developed[2] utilizing a "falling film" evaporator column which, at reduced energy requirements, provides a substantially anhydrous lower alkanesulfonic acid devoid of detectable amounts of harmful decomposition products. While this recently developed process provides much improved results, still further improvements in both the dryness of the product and productivity of the process are desirable.

[1]. See U.S. Pat. No. 4,035,242 and U.K., Pat. No. 1,350,328
[2]. See U.S. Pat. No. 4,450,047

STATEMENT OF THE INVENTION

In accordance with this invention, a process for the removal of water from a mixture of lower alkanesulfonic acid and water comprises the steps of (a) passing said mixture into a first vertical evaporator column and causing it to run down the internal surface of said column in the form of a liquid film, (b) operating said column at subatmospheric pressure and elevated temperature whereby some of the water from said mixture is vaporized as said mixture runs down said surface, (c) removing water vapor at the top and removing lower alkanesulfonic acid of reduced water content at the bottom of said column (d) passing the alkanesulfonic acid-water mixture from the bottom of said first column into a second vertical evaporator column and causing it to run down the internal surface of said second column in the form of a liquid film, and (e) repeating the manipulations of steps (b) and (c) in said second column whereby the lower alkanesulfonic acid removed at the bottom of said second column has a water content of less than 2 percent by weight.

BRIEF DESCRIPTION OF THE DRAWING

The drawing is a schematic diagram illustrating a system for carrying out the process of this invention which includes two substantially identical evaporator columns and connecting lines for operating the columns in series.

DETAILED DESCRIPTION

The present invention is a process for the facile removal of water from lower alkanesulfonic acid-water mixtures having from 1 to 8 carbon atoms, preferably 1-4 carbon atoms, in the alkane group whereby mixtures of water and such lower alkanesulfonic acids containing up to 85% by weight and higher amounts of water are treated to provide a substantially anhydrous alkanesulfonic acid product, such anhydrous alkanesulfonic acid being produced at an unexpectedly increased rate.

In the drawing, two vertically-arranged, jacketed, cylindrical, falling film evaporator columns 11 and 21 are shown. These columns may have straight walls or, as shown in the drawings, increasingly larger internal diameters from bottom to top to provide space for progressively increasing volumes of water vapor from the bottom to the top of the column. For describing the operations of these columns, a starting mixture of methanesulfonic acid (MSA) and water (e.g., 5 to 85% by weight of water) will be referred to as "the mixture". The mixture is fed from tank 17, via pump 18, to the first evaporator column 11 and distributed on the heated wall of the column by a spray ring 14 or, for example, by means as described in U.S. Pat. No. 4,450,047, column 2, first paragraph, whereby a liquid film forms and falls down the internal surface of the column. The column wall is heated to a temperature ranging between about 200° and about 350° F. (93°-175° C.), preferably between 250° and 300° F. (120°-150° C.), using, for example, steam under pressure from source 31 injected into the jacket or jackets (generally indicated by dash lines 33) surrounding the column. A mixture of a high amount of water and small amount of MSA is removed overhead via line 12 to scrubber 40. Scrubber 40 is, for example, a column packed with ceramic particles (e.g., "Intalox" porcelain saddles manufactured by the Norton Company) of suitable size and extending for a sufficient height in the scrubber column to substantially separate the MSA from the water. Part of the feed mixture from pump 18 or water can be utilized to wet the ceramic packing in scrubber 40, if required. Water vapor containing, for example, less than 0.2% by weight of MSA passes from the scrubber 40 into condenser 41 where condensation occurs. The entire system, column 11, scrubber 40 and condenser 41, are operated at reduced pressure ranging from about 10 to 200 mm of mercury (Hg) absolute (10 to 200 torr), preferably from 50 to 75 mm Hg absolute, (50 to 75 torr) supplied, for example, by vacuum system 42. The MSA-water mixture falling to the bottom of scrubber 40 is returned to feed pump 18 via line 43.

A concentrated MSA - water mixture (about 1-20% by weight water) is collected from the bottom of column 11 in tank 15 from which it is fed to the second evaporator column 21 by pump 16. The concentrated mixture is spread over the upper internal surface of column 21 by means of spray ring 24 or, for example by means as described in U.S. Pat. No. 4,450,047, column 2, first paragraph, to form a falling film of liquid. Column 21 is operated substantially under the conditions generally described for the evaporator column or columns of the aforementioned patent whereby the system is subjected to reduced pressure ranging from about 10 to 200 mm Hg (10 to 200 torr), preferably from 15 to 50 mm Hg absolute (15 to 50 torr), and an elevated temperature ranging from about 250° to 375° F. (120°-190° C.), preferably between 300° and 375° F. (150°-190° C.). To obtain the elevated temperature, steam under pressure may be supplied from 32 to the jackets surrounding column 21. Water, with a small proportion of MSA, is removed overhead and passed to condenser 51 in which it is condensed and then passed, via line 53, back to pump 18. Substantially anhydrous MSA (<2 wt. % preferably less than 0.5 wt % water) is recovered from the bottom of column 21. The product may be cooled to below 50° C. in cooler 23, collected in tank 25 and passed, via pump 26, to storage tank 27. The entire system (column 21 and condenser 51) is operated under vacuum supplied by vacuum pump 52.

The operation of evaporator columns in series provides a significant advantage over the use of a single larger evaporator column having equivalent internal wall area. In the two column arrangement disclosed herein, each column may be operated under somewhat different conditions to optimize the results. Further, by recovering most of the water after processing in the first column, a lower pressure in the second column can be attained since the use of a packed scrubber at the top of that column is obviated.

Less preferably, one or more additional evaporator columns may, if desired, be added to the system disclosed herein and operated in series with the first and second columns.

While the system used for the process of this invention is described for a mixture of MSA and water, the process may be used for other lower alkanesulfonic acid-water mixtures including, for example, mixtures containing alkanesulfonic acids having from 2 to 8 carbon atoms in the alkane group, or mixtures of these. Preferably, the process is used with alkanesulfonic acids having from 1 to 4 carbons and most preferably methanesulfonic acid.

An optional beneficial feature of the present invention is the use of a scrubber column to treat the overhead product coming from the first evaporator column. This option permits the removal of substantially sulfonic acid-free water from the system without further processing.

Another benefit of this invention is that it permits the recycling of overhead alkanesulfonic acid-water mixture midway through the process whereby separate means for treating this overhead are not required.

However, the most notable benefit provided by the process claimed herein is an unexpectedly improved recovery rate for anhydrous alkanesulfonic acid. In the process of U.S. Pat. No. 4,450,047, as shown in FIG. 3 of the patent (three evaporative columns operated in parallel), about 167 pounds per hour of substantially anhydrous methanesulfonic acid (99.5% by weight) is produced. In the process as described herein, using two evaporative columns of the same size as used in the patent but operated in series, 625 pounds per hour of a more anhydrous methanesulfonic acid is produced (99.7% by weight). It is estimated that eight additional evaporative columns would be required in the system of FIG. 3 of U.S. Pat. No. 4,450,047 to provide the same production rate of substantially anhydrous methanesulfonic acid.

We claim:

1. A process for the removal of water from a mixture of lower alkanesulfonic acid and water which comprises the steps of (a) passing said mixture into a first vertical evaporator column and causing it to run down the internal surface of said column in the form of a liquid film, (b) operating said column at subatmospheric pressure and elevated temperature whereby some of the water from said mixture is vaporized as said mixture runs down said surface, (c) removing a substance comprising water vapor at the top and removing lower alkanesulfonic acid of reduced water content at the bottom of said column, (d) passing the alkanesulfonic acid-water mixture from the bottom of said first column into a second vertical evaporator column and causing it to run down the internal surface of said second column in the form of a liquid film, and (e) repeating the manipulations of steps (b) and (c) in said second column whereby the lower alkanesulfonic acid removed at the bottom of said second column has a water content of less than 2 percent by weight.

2. The process of claim 1 wherein said first column is operated at an internal surface temperature ranging from about 93° to about 175° C. and a pressure between 10 and 200 mm Hg absolute.

3. The process of claim 2 wherein said second column is operated at an internal surface temperature ranging from about 120° to about 190° C. and a pressure between 10 and 200 mm Hg absolute.

4. The process of claim 1 wherein the substance removed from the top of said first column is a mixture of water vapor and lower alkanesulfonic acid and such mixture is subjected to a scrubbing operation to separate water from said alkanesulfonic acid.

5. The process of claim 4 wherein any lower alkanesulfonic acid-water mixture released from the scrubbing operation is recycled to said first vertical column.

6. The process of claim 1 wherein the alkanesulfonic acid has from 1 to 4 carbon atoms.

7. The process of claim 6 wherein said first column is operated at an internal surface temperature ranging from about 120° to about 150° C. and a pressure between 50 and 75 mm Hg absolute.

8. The process of claim 7 wherein said second column is operated at an internal surface temperature ranging from 150° to 190° C. and a pressure between 15 and 50 mm Hg absolute.

9. The process of claim 8 wherein the substance removed from the top of said first column is a mixture of water vapor and $C_1$-$C_4$ alkanesulfonic acid and such mixture is subjected to a scrubbing operation to separate water from said alkanesulfonic acid.

10. The process of claim 9 wherein alkanesulfonic acid-water mixture released from the scrubbing operation is recycled to said first vertical column.

11. The process of claim 10 wherein the alkanesulfonic acid is methanesulfonic acid.

12. The process of claim 10 wherein the alkanesulfonic acid-water mixture is sprayed on the internal surface at the top of said first column.

13. The process of claim 12 wherein the alkanesulfonic acid-water mixture from the bottom of said first column is sprayed on the internal surface at the top of said second column.

14. The process of claim 1 wherein said first and second columns are provided with a larger internal diameter at the top so as to provide for a larger volume of water vapor in the upper portion of each column.

15. The process of claim 10 wherein said first and second columns are provided with a larger internal diameter at the top so as to provide for a larger volume of water vapor in the upper portion of each column.

* * * * *